(12) United States Patent
Lander et al.

(10) Patent No.: US 10,946,306 B1
(45) Date of Patent: Mar. 16, 2021

(54) SOLVENT-BASED EXTRACTION METHODS

(71) Applicant: World Class Extractions Inc., Burnaby (CA)

(72) Inventors: Shane Lander, Surrey (CA); Tamas Jozsa, Chilliwack (CA)

(73) Assignee: WORLD CLASS EXTRACTIONS INC., Burnaby (CA)

( * ) Notice: Subject to any disclaimer, the term of this patent is extended or adjusted under 35 U.S.C. 154(b) by 0 days.

(21) Appl. No.: 16/697,733

(22) Filed: Nov. 27, 2019

(51) Int. Cl.
| | | |
|---|---|---|
| *B01D 11/02* | (2006.01) | |
| *C07D 311/80* | (2006.01) | |
| *C07C 39/17* | (2006.01) | |

(52) U.S. Cl.
CPC ...... *B01D 11/0284* (2013.01); *B01D 11/0265* (2013.01); *B01D 11/0288* (2013.01); *B01D 11/0292* (2013.01); *C07C 39/17* (2013.01); *C07D 311/80* (2013.01); *C07C 2601/16* (2017.05)

(58) Field of Classification Search
CPC ............ B01D 11/0284; B01D 11/0288; B01D 11/0265; B01D 11/0292; C07D 311/80; C07C 39/17; C07C 2601/16
See application file for complete search history.

(56) References Cited

U.S. PATENT DOCUMENTS

| | | |
|---|---|---|
| 8,445,034 B1 | 5/2013 | Coles |
| 10,493,377 B1 * | 12/2019 | Ferraro ................ A61K 36/185 |
| 2018/0344661 A1 * | 12/2018 | Finley .................. A61K 31/355 |
| 2019/0241536 A1 | 8/2019 | Durkacz et al. |

FOREIGN PATENT DOCUMENTS

| | | |
|---|---|---|
| CN | 104277917 | 1/2015 |
| CN | 106831353 | 6/2017 |
| CN | 106860492 | 6/2017 |

OTHER PUBLICATIONS

Azmin, M., "Herbal processing and extraction technologies." Separation & Purification Reviews 45.4 (2016): 305-320.*
Pryor, Ezra; The Perfect Solvent for Cannabis Extraction; Nov. 20, 2016; 2 pages; Cannabiz Journal.
Li, Tao et al; A Saponification Method for Chlorophyll Removal from Microalgae Biomass as Oil Feedstock; Sep. 7, 2016 (on-line https://www.ncbi.nlm.nih.gov/pmc/articles/PMC5039533/); 26 pages; Mar Drugs (Sep. 2016; 14 (9):162).
Young, Lee W.; PCT International Search Report and Written Opinion; dated Apr. 24, 2019; 8 pages; Alexandria, Virginia.
MD Range; SEEPEX Gmbh; 2019 [retrieved 2018];Retrieved from the Internet: https://www.seepex.com/us/pumps-and-control-systems/metering-pump/md-range/?no_cache=1.
Ultimate Herb Dryer; Viagrow; 2019 [retrieved 2018]; Retrieved from the Internet: https://www.atlantishydroponics.com/product-p/vuhd1.htm.
Harvester Pro Five-tier Dehydrator User Manual; Cabela; date of manual unknown [retrieved 2018]; Retrieved from Internet: https://www.cabelas.com/product/CABELAS-HARVESTER-PRO-TIER-DEHYDRATOR/2122098.uts.
ECOPURE Solvent Recyclers (Press Release); PPC Technologies & Solutions LLC; Aug. 5, 2011 [retrieved 2018]; Retrieved from Internet: https://www.ppcts.com/pr12.htm.
10 Tray Dehydrator User Manual; Cabela; Jun. 8, 2016 [retrieved 2018]; Retrieved from Internet: https://www.cabelas.com/assets/product_files/pdf/541646_Six_Tray_Heavy_Duty_Dehydrator.pdf.
Flowtron LE-900 Ultimate Mulcher Electric Leaf Shredder Owner's Manual; Flowtron; Oct. 19, 2011 [retrieved 2018]; Retrieved from Internet: https://www.flowtron.com/manuals/357%203151%20REV%2011%20LE-900%208pg%20OM.pdf.
Eco-Shredder Owners Operating Manual Chipper / Shredder / Mulcher; Durostar; Feb. 2, 2012 [retrieved 2018]; Retrieved from Internet: https://www.amleo.com/images/art/es1600-manual.pdf.
Heinkel, Inverting Filter Centrifuge HF, 2015-06-00 [retrieved 2019]; Retrieved from Internet: https://www.heinkel.com/wp-content/uploads/2018/05/HEINKEL-Inverting-HF-Series-en.pdf.

* cited by examiner

*Primary Examiner* — John M Mauro
(74) *Attorney, Agent, or Firm* — Stetina Brunda Garred and Brucker (57) ABSTRACT

Solvent-based methods for the extraction and concentration of cannabinoids and other target compounds from large-scale harvests of *cannabis* and hemp crops. Select portions of *cannabis* or hemp plants are harvested, ground to a desired particle size and ultimately powderized where the powder is mixed with a solvent, preferably ethanol or water, to form a slurry that is subjected to at least two, and preferably five or more separate inverting filter centrifugation steps until cannabinoid extraction is maximized. The filtrate from the first inverting centrifugation step is isolated and purified to derive an extract whereas the powderized filtride is subjected to further centrifugation steps. Fresh solvent is introduced at the last inverting centrifugation step and subsequently used upstream in sequentially-earlier centrifugation steps until ultimately utilized in a first inverting filter centrifugation step.

12 Claims, 4 Drawing Sheets

SOLVENT-BASED EXTRACTION METHODS

CROSS-REFERENCE TO RELATED APPLICATIONS

Not Applicable

STATEMENT RE: FEDERALLY SPONSORED RESEARCH/DEVELOPMENT

Not Applicable

BACKGROUND

The present invention relates to methods for the systematic extraction and concentration of cannabinoids and other target compounds via solvent extraction from large-scale harvests of *cannabis* and hemp crops. The methods of the present invention are very effective in maximizing the recovery of target cannabinoids, and in particular cannabidiol (CBD), from select plant structures of *cannabis* and hemp that are further exceptionally energy-efficient and conserve the volume of solvent needed to derive the desired extract.

Techniques for deriving extracts from plants, and in particular *cannabis*, are well-known in the art. Indeed, crude methods for deriving extracts from *cannabis* date back more than a thousand years ago. To that end, the primary objective in deriving such extracts is to isolate cannabinoids, namely, the chemical compounds secreted by *cannabis* that imitate naturally-produced endocannabinoids that maintain homeostasis and general health and well-being.

*Cannabis* contains at least 85 types of cannabinoids with each having a different therapeutic effect in treating pain, nausea, anxiety and inflammation, among others. When *cannabis* is consumed, whether through consumption or inhalation (as in smoking), the cannabinoids, usually following decarboxylation, are operative to bind to receptor sites either located in the brain, via CB-1 receptors, or peripherally throughout the body, via CB-2 receptors. The most well-known and studied of the cannabinoids include tetrahydrocannabinol (THC) and cannabidiol (CBD), whose respective chemical structures are shown below:

Tetrahydrocannabinol (THC)

Cannabidiol (CBD)

THC is well-known as a psychoactive or hallucinogenic compound that binds primarily to CB-1 receptors and is responsible for producing the euphoric high associated with *cannabis* consumption. CBD, on the other hand, is non-psychoactive cannabinoid and binds primarily to CB-2 receptors throughout the body and is associated with reducing anxiety, reducing pain and protecting against nerve damage, among other physiological effects.

Other known cannabinoids and their derivatives that also have potentially therapeutic applications include the following:

Cannabigerolic Acid (CBGA)
Cannabigerolic Acid Monoethylether (CBGAM)
Cannabigerolic (CBG)
Cannabigerolic Monoethylether (CBGM)
Cannabigerovarinic Acid (CBGVA)
Cannabigerovarin (CBGV)
Cannibichromenic Acid (CBCA)
Cannibichromene (CBC)
Cannibichromevarinic Acid (CBCVA)
Cannibichromevarin (CBCV)
Cannabidiolic Acid (CBDA)
Cannabidiol Monoethylether
Cannabidiol-C4 (CBD-C4)
Cannabidivarinic Acid (CBDVA)
Cannabidivarin (CBDV)
Cannabidiorcol (CBS-C1)
Delta-9-tetrahyrocannabinolic Acid A (INPLANTA A-A)
Delta-9-tetrahyrocannabinolic Acid B (INPLANTA A-B)
Delta-9-tetrahyrocannabinol (INPLANTA)
Delta-9-tetrahyrocannabinol-C4 (INPLANTA-C4)
Delta-9-tetrahyrocannabivarin (INPLANTA V)
Delta-9-tetrahyrocannabiorcolic Acid (INPLANTA A-C1)
Delta-9-tetrahyrocannabiorcol (INPLANTA-C1)
Delta-7-cis-iso-tetrahyrocannbivarin
Delta-8-tetrahyrocannabinolic Acid (8-INPLANTA A)
Delta-8-tetrahyrocannabinol (8-INPLANTA)
Cannabicyclolic Acid (CBLA)
Cannabicyclol (CBL)
Cannabicyclovarin (CBLV)
Cannabielsoic Acid A (CBEA-A)
Cannabielsoic Acid B (CBEA-B)
Cannabielsoin (CBE)
Cannabinolic Acid (CBNA)
Cannabinol (CBN)
Cannabinol Methylether (CBNM)
Cannabinol-C4 (CBN-C4)
Cannabivarin (CBV)
Cannabinol-C2 (CBN-C2)
Cannabiorcol (CBN-C1)
Cannabinodiol (CBND)
Cannabinodivarin (CBVD)
Cannabitriol (CBT)
10-Ethoxy-9-hydroxy-delta-6a-tetrahyrocannabino
8,9-Dihydroxy-delta-6a-tetrahyrocannabinol
Cannabitriolvarin (CBTV)
Ethoxy-cannabitriolvarin (CBTVE)
Dehydrocannabifuran (DCBF)
Cannabifuran (CBF)
Cannabichromanon (CBCN)
Cannabicitran (CBT)
10-Oxo-delta-6a-tetrahyrocannabinol (OINPLANTA)
Delta-9-cis-tetrahydrocannbinol (cis-INPLANTA)
3,4,5,6-Tetrahydro-7-hydroxy-alpha-alpha-2-trimethyl-9-n-propyl-2, 6-methano-2H-1-benzoxocin-5-methanol (OH-iso-HHCV)

Cannabiripsol (CBR)

Trihydroxy-delta-9-tetrahyrdocannabinol (triOH-IN-PLANTA)

Numerous studies have been and continue to be published regarding the potential therapeutic benefits of cannabinoids, including those funded by the National Institutes of Health (NIH), and the possible uses of cannabinoids for medical treatment. Indeed, based on increasing legalization of *cannabis* and advances in medical research involving cannabinoids, U.S. *cannabis* production—including licensed production of *cannabis* for marijuana and hemp—is forecast to see annual gains of over 23% through 2023. Moreover, recent market predictions estimate that the overall *cannabis* market for legal adult-use and medical sales in North America to reach $24.5 billion by 2021 and will grow to $47.3 billion 2027.

Recovering the sought-after cannabinoids from the *cannabis* plant for either recreational or medical use, however, is a challenging process. In this regard, most extraction processes require careful harvesting of select portions of the *cannabis* plant, and in particular the leaves and buds, such that once removed, such structures are subjected to a time-consuming drying process whereby the moisture content of the plant, typically around 75% moisture when harvested, is dried to have a resultant moisture content of 10-20%.

Still further, even if properly harvested and cured *cannabis* is obtained, the cannabinoids contained therein must be subjected to a separate extraction process. Many such extraction methods are well-known in the art, including simple water-based extraction, which typically utilizes water, heat and pressure through a filtering mechanism. Alternatively, cannabinoids can be derived through solvent-based extraction processes, which typically deploy the use of alcohols, such as ethanol and isopropyl alcohol, and other hydrocarbons, most notably hexane, butane and propane. Still further, supercritical carbon dioxide ($CO_2$) can be used as a solvent to derive *cannabis* extracts.

Problems associated with both water and solvent-based extraction processes are well-known. Water-based extracts are known to be significantly diluted as many of the cannabinoids are never ultimately recovered from the *cannabis* plant. Solvent-based extracts, while deriving more potent extracts, typically use toxic and potentially explosive solvents that are dangerous to store and work with. Moreover, residual solvent can and does frequently appear in the final *cannabis* extract that consequently can make the extract dangerous to consume. Both water and solvent-based extracts further suffer from the drawback of suboptimal cannabinoid extraction due to the inability to draw out intracellular cannabinoids that are typically trapped within the cell walls of the *cannabis* plant material, and hence unable to be recovered. Both extraction processes further disadvantageously can produce extracts having residual components, such as waxes, fatty acids and chlorophyll, which make for an undesirable product and require further processing to derive an extract only containing the cannabinoids of interest.

Supercritical carbon dioxide, $CO_2$, regarded by many as the most ideal solvent for extraction applications, is typically run at many times atmospheric pressure, and uses a large quantity of compressed carbon dioxide. However, several drawbacks exist with the use of $CO_2$, including the harmful effects $CO_2$ has on the environment and the high pressures and large volumes of the highly poisonous gas that must be utilized for the extraction. Engineering controls must further be in place in the event of $CO_2$ release, or else rapid suffocation is possible in the event of failure. Because of the extreme pressures involved, supercritical $CO_2$ systems must be made of pressure-rated steel, increasing the capital outlay for startup and dramatically increasing the need for diligent preventative maintenance.

Stiff further, the use of supercritical $CO_2$ causes other contaminants to be extracted along with the desired cannabinoids from the plant material, including waxes, pigments and cell-wall fragments. Thus, "winterization" is needed to obtain usable extracts, which requires dissolving the crude extract into ethanol, followed by chilling and filtering off the mass of unusable waxes, etc., and then ultimately evaporating the ethanol.

All such extraction techniques are unfortunately ill-suited for large-scale industrial extraction, particularly involving large scale commercial farming harvests where literally thousands of tons of *cannabis* and hemp plant material must be processed. Under such conditions, it will not be commercially feasible to use any kind of toxic solvent, and in particular, any type of hydrocarbon solvent such as butane or hexane, as well as supercritical $CO_2$ that is not only energy-intensive but also requires special handling and control procedures to extract cannabinoids on a large scale. Indeed, the use of any solvent in a large-scale extraction application must be highly conserved and managed in a way that maximizes the amount of cannabinoid solute dissolved therein while minimizing contaminant co-extraction and likewise allowing for solvent recycling. Moreover, any type of large-scale industrial extraction cannot involve energy-intensive contaminant-removal processing, such as winterization, that is simply not feasible for large scale batch extraction.

BRIEF SUMMARY

The present invention specifically addresses and elevates the above-identified deficiencies in the art. Specifically the present invention is directed to methods for the solvent-based extraction of cannabinoids from virtually all types of *cannabis* plant materials, including hemp, derived from large-scale commercial farming operations. In this respect, the methods of the present invention are operative to minimize energy consumption, conserve the volume of solvent utilized in the extraction process, maximize the quantity of cannabinoids sought to be extracted on a large-scale, commercial basis than other known cannabinoid extraction techniques, and in a particular prior-art solvent extraction techniques using toxic and flammable hydrocarbons or high energy consumption and capital-intensive processes, such as extraction methods using supercritical $CO_2$ coupled with winterization-type contaminant removal processes. Indeed, it is believed that the methods of the present invention are exceptionally effective for use in future applications where annually-harvested *cannabis* plant material will be produced as a bulk commodity, as future growth forecasts indicate.

With respect to the extraction processes, the same begins with the harvesting and preparation of the *cannabis* plant material. As contemplated, the *cannabis* will be harvested as part of a large-scale commercial farming operation and, once harvested, subjected to a conventional drying process. Ideally, the harvested *cannabis* plant material will be dried such that the same has a humidity less than 20%, and preferably less than 15%, with a humidity of 12% or less being most preferred.

Once sufficiently dried, the harvested plant material is subjected to a pre-chopping step to generate uniformly sized pieces of plant material ranging in size from approximately 1.0 to 3.0 inches in size. Thereafter, the pre-chopped plant material is subjected to a classification/decortication step whereby the most cannabinoid-rich plant structures, in particular, the trichomes, buds and to a lesser degree fan leaves, are isolated from the woody stock portions or hurd materials. In this respect, the plant structures most ideally targeted will have approximately 25% cannabinoid content or higher to thus ensure that cannabinoid-poor portions of the plant are not unnecessarily processed with little to no cannabinoids ultimately being extracted.

The cannabinoid-rich plant structures, once isolated, are then subjected to a grinding step such that the plant material is ground to a particle size capable of passing through screen having from 50 to 100 mesh screen size. Advantageously, such grinding step increases the surface area from which the solvent will be able to draw out the desired cannabinoids, and further facilitates the disruption of plant cell walls to thus enable intracellular contents to be extracted via the solvent. In optional steps to facilitate the storage and bulk-processing of the *cannabis* plant material once sufficiently ground, such ground plant materials may be pelletized into concentrated, space-efficient units then packaged, preferably in an inert packaging protected from light exposure, such as in sealed containers with nitrogen gas, and stored for prolonged periods of time without any type of degradation to the cannabinoids sought to be ultimately extracted. By optionally pelletizing and storing the *cannabis* material in an inert light-protected environment thus enables annually-harvested *cannabis* plant crops to be preserved and quantities processed over the calendar year and not necessarily during the actual, seasonal harvest.

Regardless if pelletized and packaged, the ground *cannabis* plant material is next subjected to a crumbling and powderization step to thus enable the cannabinoid-rich plant structures to obtain a maximum amount of surface area for cannabinoid extraction.

With respect to the actual extraction of cannabinoids from the powderized cannabinoid-rich plant components, the same is attained through at least two, and preferably a series of inverting filter centrifugation steps whereby the powderized cannabinoid-rich plant material is repeatedly mixed with a solvent, preferably ethanol or water, to form a slurry. Prior to being subjected to the inverting filter centrifugation, the slurry may optionally be subjected to ultrasound. With respect to the optional treatment with ultrasound, that may be conducted per U.S. patent application Ser. No. 16/265,768, filed Feb. 1, 2019 (pending), which relates to and claims the benefit of U.S. Provisional Application No. 62/627,616 filed Feb. 7, 2018 and entitled "METHODS FOR EXTRACTING COMPOSITIONS FROM PLANTS," the entire disclosure of each of which are hereby wholly incorporated by reference.

With respect to the inverting filter centrifugation process, such process is conventional in nature and in each case is operative to produce a solid filtride portion that comprises the solids portions of the powderization *cannabis* starting material and liquid solvent portion that is referred to as the filtrate following the first inverting filter centrifugation step and a wash corresponding to the subsequent number of times the filtride is subjected to centrifugation.

Following the first inverting centrifugation process, the filtrate is isolated and processed to remove contaminates and solvent to ultimately isolate the desired extract. The solvent is recycled for reuse. The first filtride produced thereby, which comprises the solids portion of the powderized *cannabis* plant material following the first inverting filter centrifugation step, is then mixed with solvent to form a second slurry that is subjected to a separate second inverting filter centrifugation step that ultimately produces a second wash filtrate and a second filtride.

The second filtride is again mixed with another quantity of solvent to ultimately form a third slurry that is again subjected to a third, separate inverting filter centrifugation step to produce a third wash and a third filtride, the latter of which is again mixed with solvent to form a fourth slurry that is again subjected to a separate fourth inverting filter centrifugation step to product a fourth wash and a fourth filtride.

The fourth filtride is mixed yet again with solvent to form a fifth slurry, the fifth slurry being subjected to a separate fifth inverting filter centrifugation step to produce a fifth wash of solvent and fifth filtride.

Such process where the original powderized *cannabis* plant material is repeatedly formed as a slurry, subjected to an inverting filter centrifugation step and ultimately isolated as a filtride maybe repeated as many times as desired but it is contemplated that the starting powderized material will be subjected to at least two inverting filter centrifugation cycles and in some cases ten or more cycles. In this regard, it is contemplated that so long at least 0.1% of the originally present cannabinoids can be drawn out from a given filtride through a separate inverting filter centrifugation step, such filtride maybe repeatedly formed as a slurry subjected to centrifugation and separately isolated yet again as a filtride for further centrifugation for as many cycles as necessary until such cannabinoids concentration drawn therefrom is less than 0.1%.

To advantageously conserve the solvent utilized in the processes of the present invention and maximize the amounts of cannabinoids extracted by such solvent, the present invention expressly contemplates that after several inverting centrifugations steps are initially performed, fresh or virgin solvent provided in its purest form is only introduced at the point where a given isolated filtrate will undergo its final inverting filter centrifugation. Specifically, once a filtride that has been subjected to one or more inverting centrifugation cycles is assessed to have only the minimal amounts of cannabinoids capable of being feasibly extracted (i.e., greater than or equal to 0.1% of the target cannabinoid), the fresh or virgin solvent is mixed with that filtride to form essentially a "final" slurry using that filtride that is subjected to a final inverting filter centrifugation step to yet again produce a liquid filtride or wash and a final, completely spent filtride, the latter of which is disposed of or repurposed.

The wash produced from the final inverting filter centrifugation step involving the discarded filtrate, on the other hand, is then fed upstream to sequentially earlier inverting filter centrifugation steps. For example, if a given extraction process contemplates five separate inverting filter centrifugation steps will be performed with the repeatedly centrifuged filtride being discarded following the fifth inverting filter centrifugation step, the virgin solvent will be introduced to form a slurry with that filtride that will be subjected to the fifth inverting filter centrifugation step to thus draw out what remaining cannabinoids that might be present in the previously-processed fourth filtride before the latter is discarded.

By virtue of the fact that the solvent is in its purest form, the same will thus be able to maximize the ability to draw out any remaining cannabinoids not previously removed. The solvent produced as the byproduct of the fifth inverting filter centrifugation, referred to as the fifth wash, is then subsequently fed upstream to be mixed with a separate filtride undergoing its fourth (i.e., next to last) inverting filter centrifugation step such that the fifth wash is mixed with a fourth filtride to form a fourth slurry and undergo the fourth inverting filter centrifugation relative the fourth filtride.

The fourth wash of the solvent separated by virtue of that centrifugation process is then fed upstream to form a third slurry for the third inverting filter centrifugation process relative a third filtride and so on until the original quantity of virgin solvent introduced at the final inverting filter centrifugation step relative the filtride is ultimately used to form a first slurry relative a fresh quantity of powderized *cannabis* material and thereafter processed as a filtrate from which the extracts of the present invention are derived.

As such, the solvent introduced in the process of the present invention is essentially the inverse of the powderized *cannabis* material from which the successive inverting filter centrifugation steps are performed such that the solvent utilized to form the first slurry originates from the final centrifugation step whereby a spent filtride is processed for a final time before being discarded. As a consequence, the solvent progressively becomes successively and progressively more saturated with cannabinoids as it progresses upstream through each inverting filter centrifugation step to thus pick up as many cannabinoids present in lesser concentrations before being subjected to fresh powderized *cannabis* plant material in the first slurry where the bulk of cannabinoids will most be easily drawn out in the highest concentrations given its first contact with the solvent. A maximum amount of cannabinoids are thus ultimately drawn out of the *cannabis* plant material through successive filtride washings and centrifugation steps and further, the solvent ultimately achieves a maximum saturation of cannabinoids when mixed with powderized plant material to form a first slurry and ultimately isolated as a filtrate following the first inverting filter centrifugation step relative the starting powderized *cannabis* material. That way, a single quantity of solvent essentially passes through and extracts cannabinoids through multiple passes whereby the solvent, in its purest form, is able to draw out the most diluted portions of cannabinoids and then successively draw out greater concentrations of cannabinoids until ultimately being contacted with fresh powderized plant material or maximum cannabinoids are present. Such inverted cycles ensure that every quantity of *cannabis* plant material is washed out a multiple of times with solvent and that a given quantity of solvent is successively infused multiple times with greater concentrations of cannabinoids.

While it is contemplated that different types of solvents can be utilized in the practice of the present invention, it is believed that ethanol is most highly preferred given its relatively less toxic nature and its well-known abilities to draw out cannabinoids from *cannabis* plant materials. Water is also a preferred solvent, especially due to its completely non-toxic nature, low cost, abundance and not being subject to government regulation. The use of water as the solvent also can advantageously eliminate the need for the initial drying step discussed above.

The processes of the present invention need only be practiced at room temperature and does not require any type of heating or cooling as is typical of other energy-intensive extraction processes. With respect to the relative amount solvent and plant material, it is believed that a range of 0.25 kilograms to 2.0 kilograms +/−10% by weight of plant material relative of approximately 500 milliliters +/−10% solvent is preferred with a ratio of approximately 1000 kilograms of *cannabis* plant material relative of 500 milliliters of solvent being most highly preferred for most processes. It is further believed that the range of cannabinoid concentrations sough to be extracted can range from approximately 10% or more as drawn out from *cannabis* material undergoing the first inverting filter centrifugation to a minimum amount of 0.1% from a filtride undergoing a final inverting filter centrifugation step.

BRIEF DESCRIPTION OF THE DRAWINGS

These as well as other features of the present invention will become more apparent upon reference to the drawings wherein.

DETAILED DESCRIPTION

The detailed description set forth below is intended as a description of the presently preferred embodiment of the invention, and is not intended to represent the only form in which the present invention may be implemented or performed. The description sets forth the functions and sequences of steps for practicing the invention. It is to be understood, however, that the same or equivalent functions and sequences may be accomplished by different embodiments and that they are also intended to be encompassed within the scope of the invention.

The present invention is directed to methods for extracting and concentrating desired cannabinoids from *cannabis* plant material harvested from large-scale, commercial farming operations. In this regard, the solvent-based extraction processes disclosed herein are ideally suited for, and in fact maybe the only practical methods by which the anticipated huge volumes and tonnage of *cannabis* plant material grown commercially can be realistically processed given the projected hundreds of thousands of acres that will be dedicated for outdoor *cannabis* growing operations.

Figure 1:
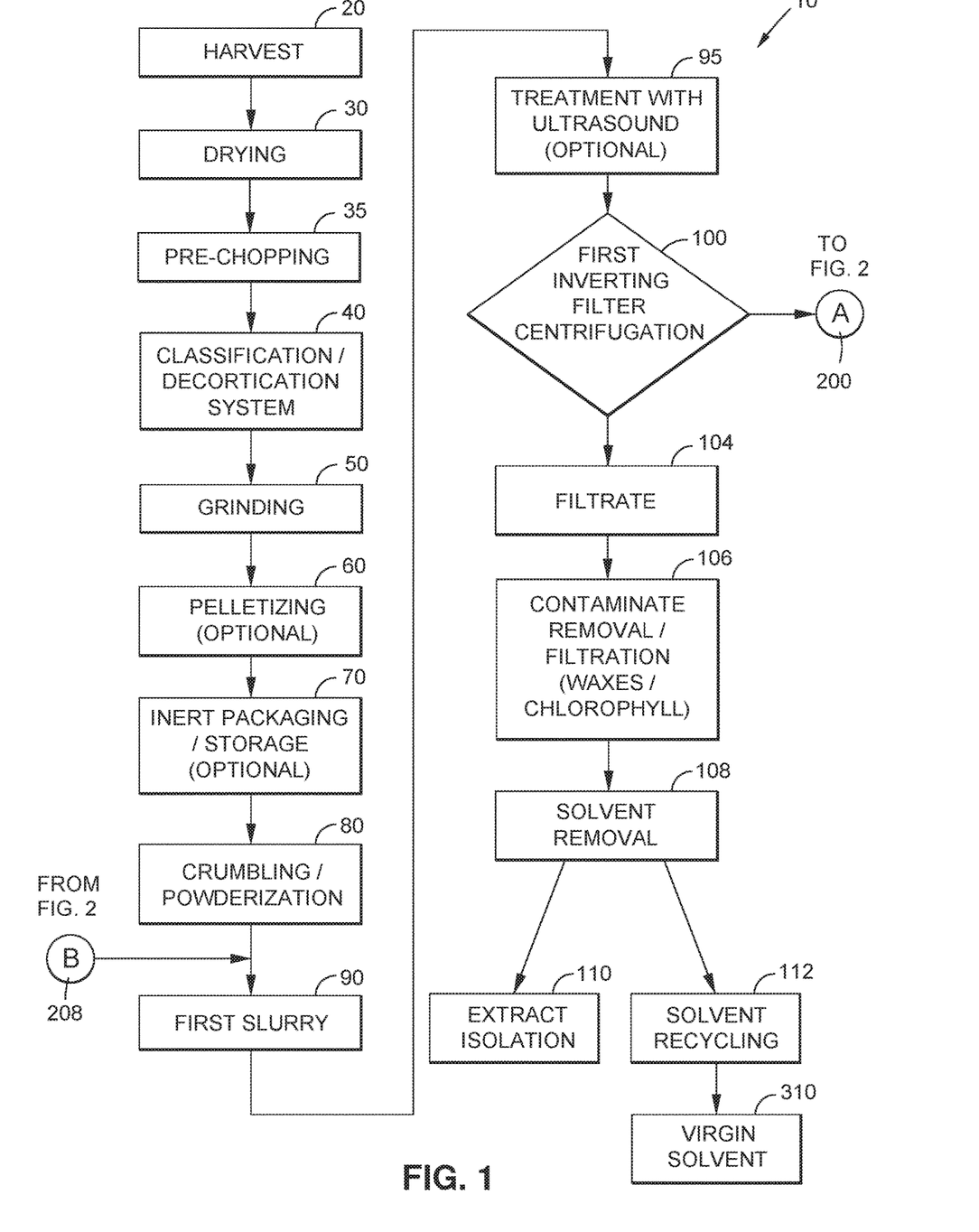
FIG. 1 is a flowchart depicting the sequential steps for preforming the initial steps for deriving a botanical extract according to a preferred method of the present invention.

To that end, and referring to the drawings and initially to FIG. 1, there is shown a process 10 for deriving extracts from commercially harvested *cannabis* according to a preferred embodiment of the present invention. While it is believed that any variety of well-known *cannabis* plants can be processed thereby, and in particular either *cannabis indica* or *Cannabis sativa*, it should be understood that for purposes of the present invention, the term "*cannabis*" should be construed to encompass all species of *cannabis*, including sub-species, i.e., *indica, sativa, ruderalis*, and expressly includes hemp and all parts thereof as presently defined as containing >0.3% THC per volume concentration. It is further emphasized that the term "*cannabis*" may include specific varieties of *cannabis* that maybe chosen based upon the desired cannabinoid sought to be derived, as well as combinations of cannabinoids, terpenes or any other profile of compounds sought to be targeted and extracted from one or more varieties of *cannabis*.

The initial step of the process 10 includes the conventional harvesting 20 of the desired *cannabis* plant material, which can be performed by any of a variety of techniques known in the art or later developed. For purposes of the present invention, and as discussed more fully below, harvesting step 20 will include any and all portions of the *cannabis* plant but ideally will concentrate on those portions of the *cannabis* plant believed to be rich in the desired cannabinoid sought to be extracted, with structures such as trichomes, sugar leaves and mature buds/calyx being deemed the most prized portions of the plant, followed by fan leaves and stems, and then by the undesirable plant structures, such as the stock and pistils that, for cannabinoids such as THC, have little to no concentrations of such cannabinoids.

Once harvested, the *cannabis* plant is then dried in step 30 to remove as much moisture from the plant as is practical. To that end, it is believed that the plant material should be dried to a humidity of less than 20%, and more preferably less than 15% with less than 12% humidity being most preferred. Such step of drying 30 can be accomplished through any variety of known techniques in the art utilizing conventional technology now available or later developed. As should be understood, however, because of the susceptibility many cannabinoids to thermally degrade, care should be taken such that the step of drying 30 is practiced in a manner that minimizes the use of heat and to preserve the intact plant as much as possible.

Following drying step 30, the plant material is pre-chopped at step 35 to generate pieces of plant material of generally uniform size. Preferably, the pre-chopping step, which may be performed with any of a variety of conventional agricultural cutting or shredding equipment, will be operative to general plant material having at least one dimension ranging from approximately 1 to 3 inches long.

A classification/decortication system step 40 is then performed whereby the most desired cannabinoid-rich portions of the harvested *cannabis* plant, such as buds/flowers of the female *cannabis* plant, are identified and isolated. In this regard, such step 40 maybe practiced by any of variety of conventional techniques known in the art or later developed that focus on separating the highly-valued, cannabinoid-rich portions of the plant from stocks or other tough, woody portions of the plant (i.e., the hurd material). Removing those portions of the *cannabis* plant that are devoid of cannabinoids is believed to be a key factor in the practice of the present invention insofar as significant inefficiencies would be introduced when practicing such methods, discussed more fully below, whereby highly conserved amounts of solvents are utilized to extract a maximum degree of cannabinoids. Processing plant material having little to no cannabinoids would consequently yield little to no benefit.

The cannabinoid-rich portions of the harvested plant that are obtained following step 40 are then subjected to grinding in step 50 to increase the surface area of the plant material that may be to subjected to the extraction process, as well as to facilitate the tearing and opening of cell walls to allow intracellular contents to be more readily accessed. To that end, it is believed that the step of grinding should be performed such that the plant material is ultimately capable of passing through a 50 to up to 100 mesh screen.

In further optional steps 60 and 70, it is contemplated that the material ground in step 50 maybe processed in a manner that facilitates the long-term preservation and storage of such *cannabis* plant material to the extent market conditions, seasonal growing conditions and crop yields, and other factors dictate possible stockpiling of such desirable *cannabis* plant materials for future processing, per conventional agricultural practices, as opposed to risking that the seasonal harvested *cannabis* material become perishable prior to extraction. In this regard, the present invention expressly contemplates the large-scale commercial production of *cannabis* plant material and that the harvested plant materials will eventually become a commodity with the production of the *cannabis* plant extracts taking place year-around and not limited to any specific outdoor growing season. Advantageously, the methods of present invention are ideally suited for treating and extracting large volumes of *cannabis* plant material at the time of harvest but also can be deployed to produce cannabinoid-rich extracts from stored plant material regardless of the growing season depending on commercial demand.

Steps 60 and 70 facilitate that outcome by preserving the *cannabis* ground in step 50 by deploying a first pelletizing step 60 to compress the ground *cannabis* material in a space efficient manner that can be easily stored and handled. Such pelletizing techniques are known in the art and routinely practiced. When in such pelletize form 60, the same maybe packaged, preferably in a sealed, light-sensitive, inert environment by utilizing materials such as nitrogen gas and the like, to minimize any potential degradation of the cannabinoids that may occur by virtue by being in storage for a long period of time. Such optional steps 60 may be performed by any of a variety of techniques or packaging methods known or later developed in the art.

Ultimately, the ground *cannabis* material in step 50, whether or not produced directly from the grinding process 50 or removed from optional packaging and in its pelletized form, is ultimately subjected to a crumbling/powderization step 80 to thus maximize the surface area of the *cannabis* material and prepare the same for the solvent-based extraction processes discussed below. With respect to the crumbing/powderization step 80, the same may likewise be performed according to any variety of techniques known or later developed in the art.

As for the extraction of cannabinoids from the powderized *cannabis* material generated in step 80, the present invention expressly contemplates that such extraction will occur whereby a discreet quantity of powderized *cannabis* material will be repeatedly mixed with a solvent, the latter being operative to draw out the desired cannabinoids from the solid plant material via an inverting filter centrifugation step, separating the solvent from the solids portions, referred to as a filtride, and then re-subjecting that same filtride to another quantity of solvent for at least one further inverting filter centrifugation cycle but as many cycles as needed until such time as little to no practical amounts of cannabinoids can be drawn out of that discreet portion of the original starting powderized *cannabis* material.

To perhaps better conceptualize the concepts behind the present invention, a very rough analogy can be made to the use of a single tea bag to make multiple cups of tea. The first cup of tea will obviously produce the strongest cup of tea as the soluble components of the tea leaves have not yet before been extracted by water. Following the first cup of tea, the same tea bag will be used to make a second cup of tea that is weaker than the first by virtue of the fact that many of the soluble components were previously removed; however, some soluble components will still remain and operative to diffuse into the water. When the same tea bag is used yet again for a third cup, some soluble components of the tea leaves will still be present, albeit in lesser concentration, and thus will make a further diluted cup of tea. The process continues until such time until all meaningful levels of soluble components of the tea leaves have been extracted in prior cups and the solids portions of the remaining tea leaves being depleted of any soluble components to make tea.

An inverse principal is applied with respect to the solvent utilized in the extraction steps of the present invention. For the solvent portion, and again using the aforementioned analogy of making tea to help better explain the concepts of the present invention, it is contemplated that when multiple tea bags are sequentially used to make tea, the water used to make each cup will be stronger of more diluted depending on the number of times the tea bag has been used.

For this analogy, a quantity of fresh water will be utilized to make the last cup of tea from the spent tea bag (i.e., the one that has been utilized numerous times before). So, fresh water would be utilized with a tea bag that may have been used two, three, four, five or more times before with very few remaining soluble components present in the tea leaves. Whatever soluble components are present, however, are most easily removed and dissolved into the quantity of fresh water that has no other soluble components dissolved therein. Accordingly, there is no saturation point that would prevent soluble components from otherwise dissolving into the water.

The present invention contemplates that the liquid portion from that "final" cup of tea is set aside and used sequentially in an upstream manner to make cups of tea from tea bags that have been utilized less times. For example in this analogy, if a teabag is to be utilized to make five cups of tea, fresh water will be utilized to make the fifth or last cup of tea to draw out what remaining soluble components exist before the tea bag is discarded, and then that diluted tea then utilized with another tea bag being utilized to make a fourth cup of tea to thus draw out more soluble compounds then had been drawn out of the prior tea bag. The solvent is then sequentially caused to become more and more concentrated with soluble components until ultimately utilized with a fresh, unused tea bag.

Because the water has been previously mixed with tea bags having been utilized two, three, four, and five times, respectfully, the water or liquid tea portion becomes more and more saturated with the soluble components of the successive tea bags until subjected to a fresh, unutilized tea bag where a maximum amount of soluble components will be caused to dissolved into the water that advantageously has as many other soluble components that were capable of being drawn out of other sequentially-utilized tea bags. In every case, each quantity of solvent is thus utilized a maximum amount of times starting from its purest form to draw out the most resistant soluble compounds to a most saturated state when utilized with fresh, unused tea.

Figure 2:
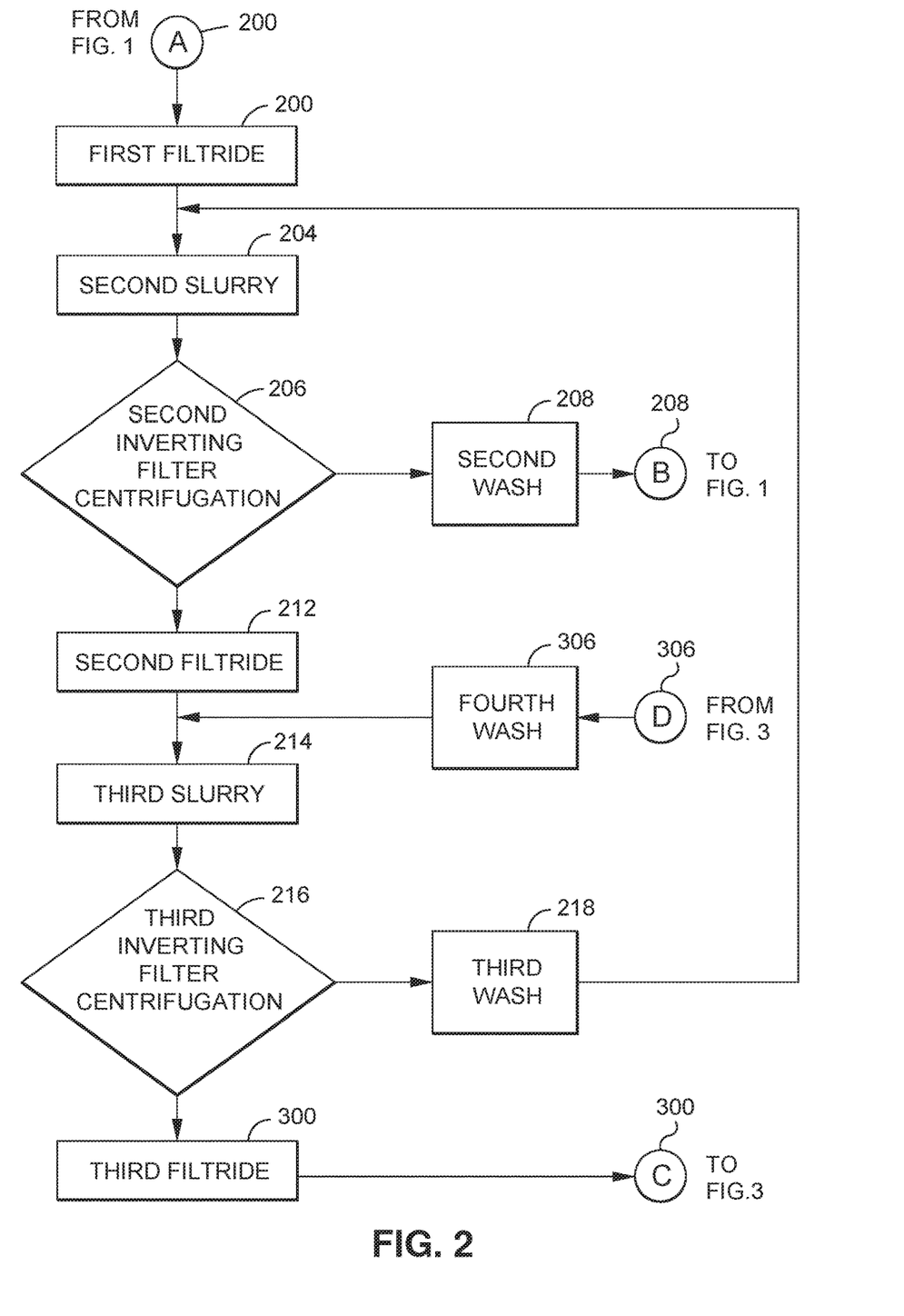
FIG. 2 is a continuation of the flow chart of FIG. 1 showing additional steps for preforming the botanical extraction methods according to the preferred embodiment of the present invention.
Figure 3:
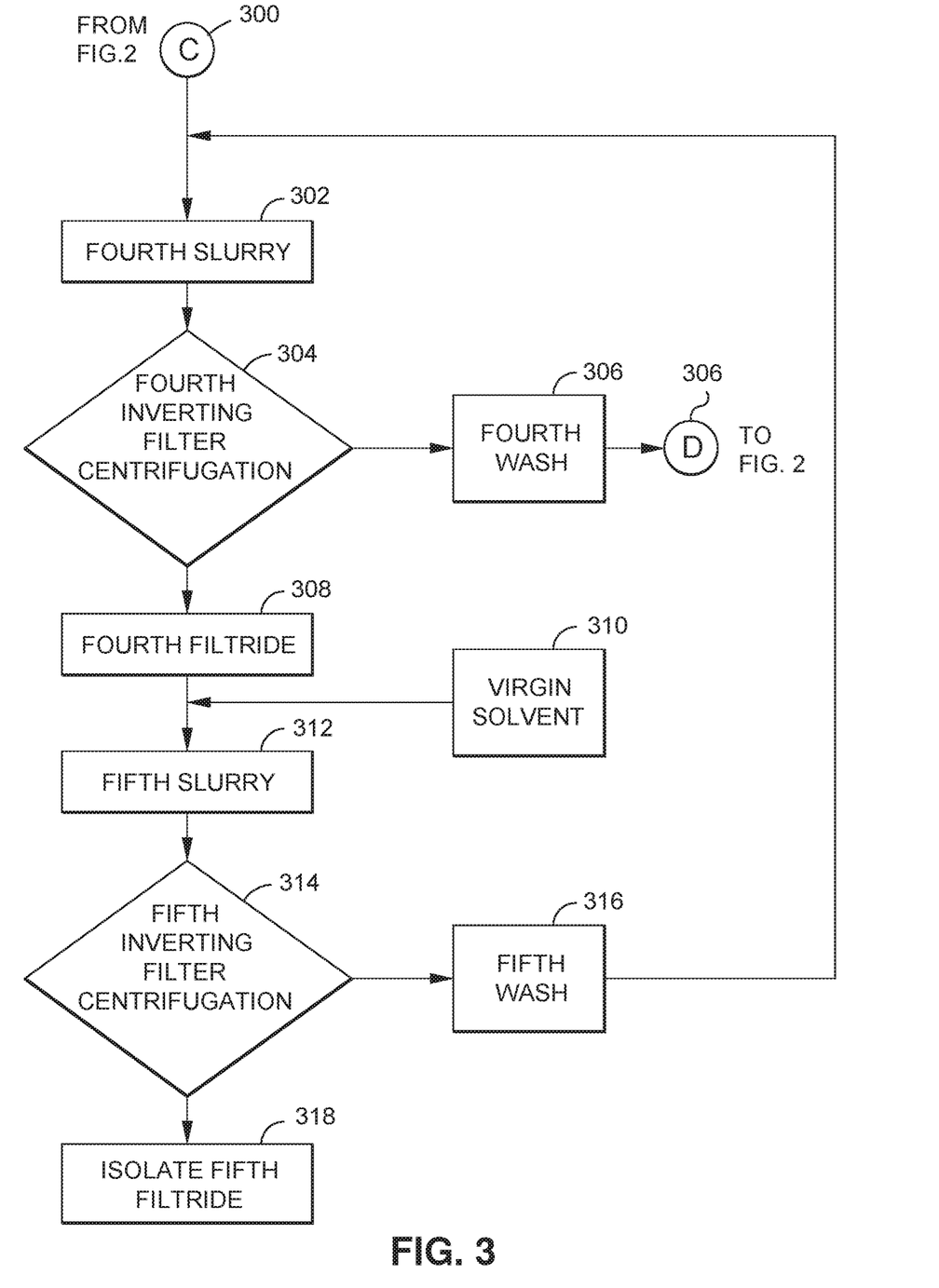
FIG. 3 is a continuation of the flow chart of FIG. 1 showing the remaining steps of a botanical extraction method according to a preferred embodiment of the present invention.

Bearing that foregoing general explanation in mind, and continuing on with reference to FIGS. 1-3, there is shown how the systematic deployment of the methods of the present invention are operative to sequentially extract cannabinoids from the starting powderized material in step 80 through a series of repetitious solvent extraction processes. Such solvent extraction processes essentially involves the use of a quantity of solvent that is mixed with a relative amount of powderized *cannabis* material to form a slurry that is then subjected to an inverting filter centrifugation process to ultimately produce a liquid filtrate or wash, on one-hand, and a solid or filtride portion on the other hand. Such solvent may be selected from any variety of known solvents, including those in the group consisting of ethanol, butane, propane, isopropyl alcohol, coconut oil, glycerin, propylene glycol, naphtha or water.

Based upon its substantially lesser degree of toxicity, effectiveness at drawing out cannabinoids from *cannabis* plant material, commercial availability and cost of materials, it is believed that ethanol is the superior solvent for use in the practice of the present invention. Water is likewise believed to be a superior solvent given the fact it is completely non-toxic, abundant, inexpensive and not subject to government regulation. Water is further advantageous insofar as its use as a solvent in the practice of the present invention can eliminate the need for the drying step 30 as discussed above and thus can allow freshly harvested *cannabis* to be processed immediately after harvesting.

With respect to the relative amounts of powderized *cannabis* plant material relative to solvent, it is contemplated that a range of 0.25 kilograms to 2.0 kilograms of *cannabis* material produced in 80, +/−10%, will be mixed per 500 milliliters of solvent, +/−10%. In a more highly preferred embodiment, it is believed that a ratio of approximately 1,000 kilograms of powderized *cannabis* material to approximately 500 milliliters of solvent will produce the most efficient extraction. Such components will be mixed with one another per conventional mixing techniques, typically within a conventional slurry tank for a duration of approximately 15 minutes or less until a uniformed slurry is formed. Advantageously, the formation of a slurry may be conducted at room temperature, although the formation of slurries at temperatures ranging from −20° C. to 50° C. are believed to have no determinantal effect on the extraction processes of the present invention.

When fresh powderized *cannabis* material produced in 80 is mixed with a relative amount of solvent as discussed above, there is formed a first slurry 90, as shown in FIG. 1. In an optional step 95, such slurry may be subjected to ultrasound to help facilitate the breakdown of cell walls and other plant structures to thus increase the release and ultimate recovery of cannabinoids. Such option step 95 may be performed pursuant to Applicants' co-owned U.S. patent application Ser. No. 16/265,768, filed Feb. 1, 2019 (pending), which relates to and claims the benefit of U.S. Provisional Application No. 62/627,616 filed Feb. 7, 2018 and entitled "METHODS FOR EXTRACTING COMPOSITIONS FROM PLANTS," the entire disclosure of each of which are hereby wholly incorporated by reference.

Whether or not treated with ultrasound at step 95, the slurry is then subjected to a first inverting filter centrifugation process 100. In this respect, as the powderized *cannabis* material has not yet been before processed for extraction, such step 100 is deemed to be the first inverting filter centrifugation step. With respect to such inverting filter centrifugation step 100, the same may be conducted in any variety of known conventional systems, including horizonal inverting centrifugation systems well-known in the art. Exemplary of such systems include the Inverting Filter Centrifuge HF produced by Heinkel Drying & Separation Group of Besigheim, Germany that is operative to process substantial quantities of slurry to thus process large-scale quantities of *cannabis*.

As a result of the first inverting filter centrifugation process 100, there is produced a first filtride 200 referenced as A in FIG. 1 and extending to FIG. 2, and a filtrate portion 104. With respect to the latter, such filtrate 104 is the basis from which the extracts are ultimately derived through the practice of the present invention. To that end, the filtrate 104 is processed to remove containments, such as waxes and chlorophyll in step 106. Along those lines, it is contemplated that any of a variety of known filtering systems for removing chlorophyll or the like maybe deployed in the practice of the present invention, such as membrane filtration techniques in combination with activated carbon. Conventional winterization steps may also be deployed whereby sufficiently chilling the filtrate will enable fats and waxed to agglomerate and thus be more easily removed using known techniques.

Thereafter, in step 108, the solvent is removed, which may likewise be accomplished by a variety of known techniques in the art, such as by vacuum distillation or wiped-film evaporative oil-solvent separation processes well-known and extensively practiced in the art. Ultimately produced is an isolated extract at 110 and the solvents separated therefrom in step 112, the latter being recycled per conventional mechanisms known in the art such as through the deployment of fractionating columns and vacuum recovery. The purified recycled solvent, referred to as virgin solvent 310, may then be reused to generate further extracts discussed below.

The first filtride 200, produced as a byproduct of the first inverting filter centrifugation step 100, is then mixed with another quantity of solvent to form a second slurry 204 as shown in FIG. 2. As discussed above, the amount of filtride relative amount of solvent will range from between 0.25 kilograms to 2.0 kilograms +/−10% per 500 milliliters of solvent +/−10% with approximately 1,000 kilograms of filtride per approximately 500 milliliters of solvent being preferred. The resultant in slurry 204 is prepared as discussed above and then subjected to a second inverting filter centrifugation 206 that will consequently produce a second wash 208, the latter corresponding to element B for use in an upstream slurry formation and inverting filter centrifugation process shown in FIG. 1 and a second filtride 212. As discussed above, by virtue of having been subjected to a second quantity of solvent, formed as a slurry and subjected to a second inverting filter centrifugation 206, additional quantities of cannabinoids present in the original powderized *cannabis*, which now becomes a second filtride, have been removed therefrom.

Notwithstanding, such second filtride 212 is yet again mixed with a quantity solvent to form a third slurry 214, which per the steps described above, is subjected a third inverting filter centrifugation step 216 that ultimately produces a third wash 218 and third filtride 300. With respect to the third wash 218, the same is used in an upstream fashion for use with a first filtride generated from a separate quantity of powderized *cannabis* material where the third filtride 300, represented as C extending from FIG. 2 to FIG. 3, is yet again mixed with a quantity of solvent to form a fourth slurry 302 that is subjected yet again to a fourth inverting filter centrifugation 304, that in turn produces a fourth wash 306 and fourth filtride 308.

In the practice of present invention, it is believed that as many inverting filter centrifugation steps may be sequentially practiced for any given quantity of starting powderized *cannabis* material, similar to the tea bag analogy discussed above, until such time that it is no longer desired or impractical to draw out any further cannabinoids from the starting powderized *cannabis* material. In order to effectively and efficiently practice the methods of the present invention, it is believed that the inverting centrifugation steps should be performed until such time as 0.1% or less of the target cannabinoids sought to be extracted is being drawn out from a given filtride, whether it is the second filtride, third filtride, ninth filtride or twentieth filtride as produced from consecutive inverting filter centrifugation processes. Along those lines, it is believed that the corresponding wash generated as a byproduct from a given inverting filter centrifugation process may be readily analyzed using techniques well-known in the art to determine the quantity or concentration of the targeted cannabinoid drawn out by the solvent following a specific centrifugation step to determine whether or not the threshold levels of cannabinoids have been meet. To the extent that they have not, a given filtride can be repeatedly processed or, as discussed in FIG. 3, processed a final time whereby a starting quantity of solvent, represented as virgin solvent 310, is mixed with the fourth filtride 308 to form fifth slurry 312, per the teachings described above, and subjected to a fifth inverting filter centrifugation 314, to produce a fifth wash 316 and a final fifth filtride 318. Such filtride 318 maybe discarded or repurposed as may be desired for a given application, including possibly palletized of use in fuel applications or any other uses known or later developed in the art.

In all cases, though, every quantity of powderized *cannabis* material will ultimately be subjected to repeated washings and extractions that ensure that the maximum amount of cannabinoids are derived therefrom using the same series of steps, the same equipment, and the same quantity of solvent in redundant manner that in turn minimizes the scale of the processing operations, the capital necessary to perform the extraction procedures, and most importantly, substantially conserves the amount of solvent utilized to achieve a maximum extraction of cannabinoids from a given amount of *cannabis* plant material.

Figure 4:
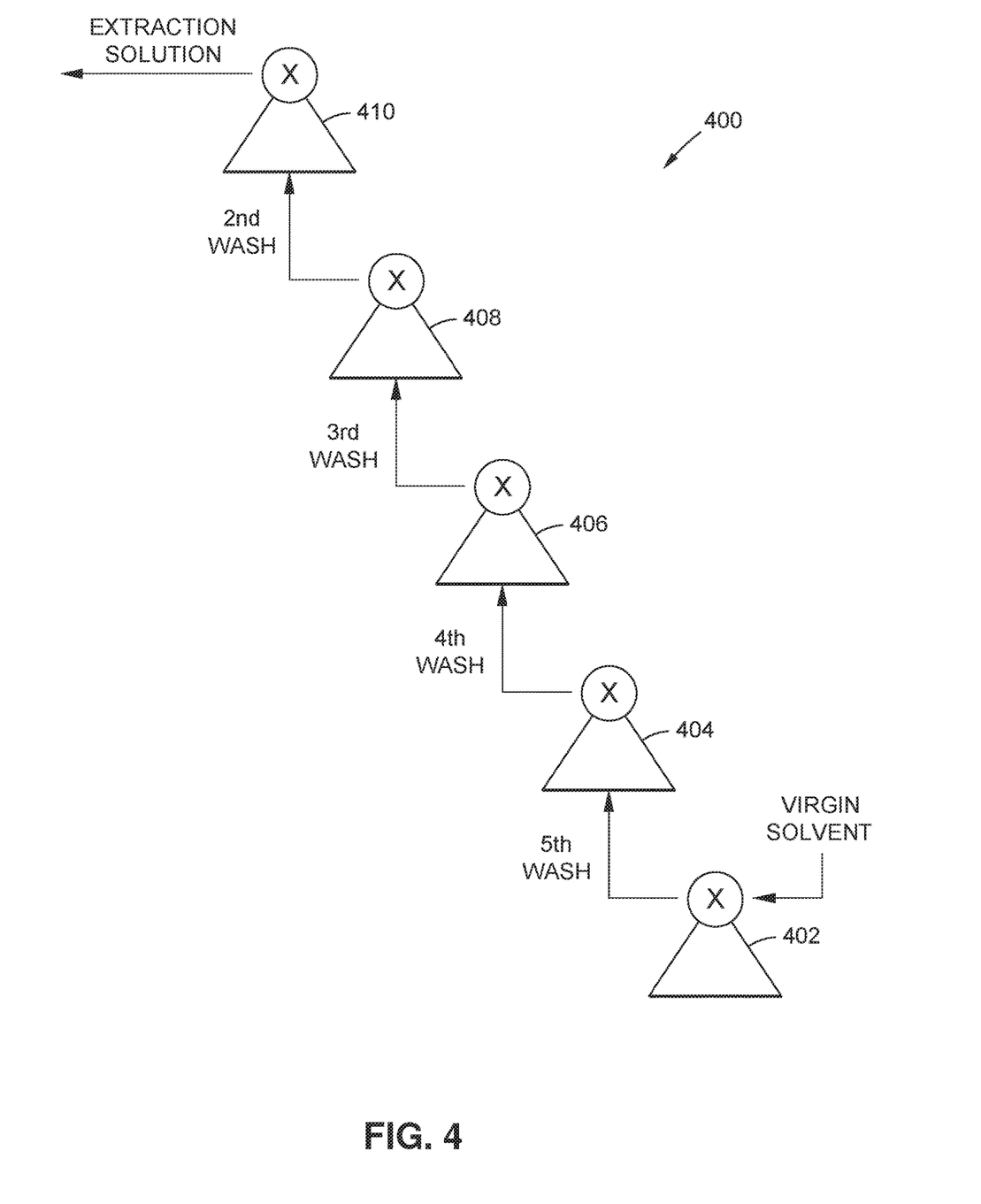
FIG. 4 is a flow chart depicting the introduction of fresh, virgin solvent and its use in successive inverting filters subjugation steps to ultimately produce an extraction solution filtrate from which an extract is ultimately derived.

With respect to the latter aspect of the invention, there is conceptionally illustrated in FIG. 4 the process by which a given quantity of solvent is introduced in a series of extraction cycles 400. As should be understood, before the solvent-conserving steps of the present invention can be realized, it will be understood that for at least the first quantity of powderized *cannabis* that is serially processed through the sequence of inverting filter centrifugation steps that each respective slurry that is formed may be made with fresh, undiluted virgin solvent (which may comprise recycled solvent generated in step 112) with the quantity of solvent utilized for the last inverting filter centrifugation step being the point of introduction where such quantity of solvent can begin to be utilized upstream starting with the final inverting filter centrifugation step and ultimately to a first inverting filter centrifugation step that will produce the filtrate deriving the extracts of the present invention.

Unlike the powderized *cannabis* that is serially processed and subsequently forms first filtrides, second filtrides, third filtrides and so on, the solvent is introduced at the last inverting filter centrifugation step, shown as 402, that generates the fifth wash as a byproduct and utilized in a fourth inverting filter centrifugation step 404 to ultimately produce a fourth wash used in an earlier inverting filter centrifugation step 406, and again to produce a third wash used in second inverting filter centrifugation step 408, thus producing a second wash that is utilized in a first inverting filter centrifugation step 410, the latter of which ultimately producing the liquid filtrate from which the extracts are derived.

As discussed above, the solvent, in its purest and undiluted form, is mixed with the filtride having the least amount of cannabinoids present to maximize what remaining extraction of those cannabinoids that can be obtained. As the quantity of solvent works upstream in further centrifugation steps, the solvent becomes further saturated with the desired cannabinoids that are correspondingly easier to draw out given their greater concentration relative the earlier filtrides that are mixed with the solvent. As such, it is believed that by the time the second wash is utilized in a first inverting filter centrifugation step, the most easily and readily extractable cannabinoids will be drawn into the solvent by virtue of the inverting centrifugation process using starting *cannabis* powder such that even if not maximized, the second wash will have at least picked up as many cannabinoids as is possible from earlier centrifugation steps such that a maximum amount of cannabinoids are ultimately isolated for further use, as opposed to any type of suboptimal extraction procedures that result in the disposal of the *cannabis* material while still bearing valuable quantities of desired cannabinoids. The present invention substantially eliminates such waste.

Additional modifications and improvements of the present invention may also be apparent to those of ordinary skill in the art. For example, while the optional step of applying ultrasound 95 is shown prior to the first inverting filter centrifugation step 100, the application of ultrasound could be deployed to any slurry, such as second slurry 204, third slurry 214, fourth slurry 302 and/or fifth slurry 312 prior to being subjected to inverting centrifugation. Thus, the particular combination of parts and steps described and illustrated herein is intended to represent only certain embodiments of the present invention, and is not intended to serve as limitations of alternative devices and methods within the spirit and scope of the invention.

What is claimed is:

1. A method for extracting cannabinoids from *cannabis* plant material comprising the steps:
   a) providing a first quantity of *cannabis* plant material and a first quantity of solvent;
   b) mixing said first quantity of *cannabis* plant material and said first quantity of solvent to form a first slurry, whereby a portion of the cannabinoids present in said first quantity of *cannabis* plant material is transferred to said first quantity of solvent;
   c) separating the solids portion and the liquid portion of said first slurry produced in step b) via inverting filter centrifugation, said solids portion defining a first filtride and said liquid portion defining a first filtrate;
   d) removing impurities from said first filtrate separated in step c) to produce a purified filtrate;
   e) isolating at least a portion of said portion of cannabinoids transferred to said first quantity of solvent in step b) from said purified filtrate produced in step d);
   f) mixing said first filtride separated in step c) with a second quantity of solvent to produce a second slurry whereby a second portion of cannabinoids still present in said filtride are transferred to said second quantity of solvent;
   g) separating the solids portion and the liquid portion of said second slurry produced in step f) via inverting filter centrifugation, said solids portion defining a second filtride and liquid portion defining a first wash;
   h) providing a second quantity of *cannabis* plant material and mixing said second quantity of *cannabis* plant material with said first wash produced in step g) to form a third slurry whereby a portion of the cannabinoids present in said second quantity of *cannabis* plant material are transferred to said first wash;
   i) separating the solids portion and the liquid portion of said first wash produced in step h) via inverting filter centrifugation, said solids portion defining a third filtride and said liquid portion defining a second filtrate;
   j) removing impurities from the second filtrate produced in step i) to produce a purified second filtrate; and
   k) isolating at least a portion of said portion of cannabinoids transferred to said first wash in step h) from said purified second filtrate produced in step j).

2. The method of claim 1 wherein at least one of steps b), f) and h) further include subjecting said first, second, or third slurry to ultrasound.

3. The method of claim 1 further comprising the steps following step k):
   l) mixing said second filtride separated in step g) with a third quantity of solvent to produce a fourth slurry whereby a portion of cannabinoids still present in said second filtride are transferred to said third quantity of solvent;
   m) separating the solids portion and the liquid portion of said fourth slurry produced in step l) via inverting filter centrifugation, said solids portion defining a fourth filtride and said liquid portion defining a second wash;
   n) mixing said fourth filtride separated in step m) with a fourth quantity of solvent to produce a fifth slurry whereby a portion of cannabinoids still present in said fourth filtride are transferred to said fourth quantity of solvent;
   o) separating the solids portion and the liquid portion of said fourth slurry produced in step m) via inverting filter centrifugation, said solids portion defining a fifth filtride and said liquid portion defining a third wash;
   p) mixing said fifth filtride separated in step o) with a fifth quantity of solvent to produce a sixth slurry whereby a portion of cannabinoids still present in said fifth filtride are transferred to said fifth quantity of solvent;
   q) separating the solids portion and the liquid portion of said sixth slurry produced in step p) via inverting filter centrifugation, said solids portion defining a sixth filtride and said liquid portion defining a fourth wash;
   r) mixing said sixth filtride separated in step q) with a sixth quantity of solvent to produce a seventh slurry whereby a portion of cannabinoids still present in said filtride are transferred to said sixth quantity of solvent; and
   s) separating the solids portion and the liquid portion of said seventh slurry produced in step p) via a inverting filter centrifugation.

4. The method of claim 2 wherein in step r), said sixth quantity of solvent comprises a virgin solvent.

5. The method of claim 4 wherein said method further comprises the step following step s):
   t) discarding the solids portion separated in step s).

6. The method of claim 3 wherein in steps b), f), h), and l), said *cannabis* plant material and said filtrides are mixed in amount from 0.25 to 2.0 kilograms, +/−10%, to 500 milliliters of solvent, +/−10%.

7. The method of claim 6, wherein said solvent is selected from the group consisting of ethanol and water.

8. The method of claim 7 wherein in step b), said *cannabis* plant material and said first quantity of solvent are mixed in an amount of approximately 1.000 kilogram of *cannabis* plant material to approximately 500 milliliters of solvent.

9. The method of claim 4 wherein in steps b), f), l), n), p) and r), said mixing occurs for a duration of 15 minutes or less.

10. The method of claim 3 further comprising the step of mixing said second wash produced in step m) with at least one filtride to form a second wash slurry, said at least one filtride comprising the solids portion of a quantity of *cannabis* plant material previously subjected to and isolated from an inverting filter centrifugation process, and subjecting said second wash slurry to further inverting filter centrifugation.

11. The method of claim 3 further comprising the step of mixing said third wash produced in step o) with at least one filtride to form a third wash slurry, said filtride comprising the solids portion of a quantity of *cannabis* plant material previously subjected to and isolated from an inverting filter centrifugation process, and subjecting said third wash slurry to further inverting filter centrifugation.

12. The method of claim 3 further comprising the step:
t) mixing said fourth wash produced in step q) with at least one filtride to form a fourth wash slurry, said filtride comprising the solids portion of a quantity of *cannabis* plant material previously subjected to and isolated from an inverting filter centrifugation process, and subjecting said fourth wash slurry to further inverting filter centrifugation.

* * * * *